(12) United States Patent
Klee et al.

(10) Patent No.: US 7,041,709 B2
(45) Date of Patent: May 9, 2006

(54) DENTAL ADHESIVE COMPOSITION

(75) Inventors: Joachim E. Klee, Radolfzell (DE); Uwe Lehmann, Constance (DE); Uwe Walz, Constance (DE)

(73) Assignee: Dentsply DeTrey GmbH, Constance (DE)

( * ) Notice: Subject to any disclaimer, the term of this patent is extended or adjusted under 35 U.S.C. 154(b) by 326 days.

(21) Appl. No.: 10/341,985

(22) Filed: Jan. 14, 2003

(65) Prior Publication Data

US 2003/0187094 A1    Oct. 2, 2003

(51) Int. Cl.
C08J 3/28    (2006.01)

(52) U.S. Cl. .......................... 522/99; 522/37; 522/43; 522/64; 523/109; 523/223; 524/379; 524/858; 528/30; 556/404; 556/405; 556/413; 556/418; 556/419; 556/427; 556/428

(58) Field of Classification Search .................. 528/30; 524/588; 556/404, 405, 413, 418, 419, 427, 556/428; 523/109, 223
See application file for complete search history.

(56) References Cited

U.S. PATENT DOCUMENTS

| | | | |
|---|---|---|---|
| 3,122,581 A * | 2/1964 | Pike | 556/405 |
| 3,507,897 A * | 4/1970 | Pike et al. | 516/55 |
| 3,660,452 A * | 5/1972 | Morehouse | 556/423 |
| 5,705,665 A * | 1/1998 | Ichinohe et al. | 556/428 |
| 6,743,936 B1 * | 6/2004 | Wellinghoff et al. | 556/405 |

| | | | |
|---|---|---|---|
| 2004/0098243 A1 * | 5/2004 | Kinsey | 703/22 |

FOREIGN PATENT DOCUMENTS

| | | |
|---|---|---|
| DE | 198 16 148 | 10/1999 |
| EP | 1 022 012 | 7/2000 |
| EP | 1 057 468 | 12/2000 |
| EP | 1 169 996 | 1/2002 |
| WO | 98/28307 | 7/1998 |
| WO | 01/08639 | 2/2001 |
| WO | 03/013444 | 2/2003 |

OTHER PUBLICATIONS

Partial abstract for an article entitled "Synthesis of Aminopropyltriethoxysilane-Catalyzed Organsilica Hybrid Nanoparticles" appearing in Polymer Preprints (american Chemical Society, Division of POlymer Chemistry) 2000,41(2) 1356.*

* cited by examiner

Primary Examiner—Marc S. Zimmer
(74) Attorney, Agent, or Firm—Daniel W. Sullivan; James B. Bieber; Douglas J. Hura

(57) ABSTRACT

A composition including nanoparticles each having an acidic polymerizable siloxane moiety. For example, a hydrolysis stable, self-etching, self-priming dental adhesive composition including 90 to 10 percent by weight of an aqueous phase, and 10 to 90 percent by weight of acidic polymerizable nanoparticles. The acidic polymerizable nanoparticles are obtainable by hydrolysis of a mixture containing one or more hydrolyzable organosilicon compounds wherein (i) at least a portion of the hydrolyzable organosilicon compounds contains one or more polymerizable groups and (ii) at least a portion of the hydrolyzable organosilicon compounds contain one or more acidic moieties.

35 Claims, No Drawings

DENTAL ADHESIVE COMPOSITION

The invention relates to hydrolysis stable, self-etching, self-priming dental adhesive compositions. The invention provides nanoparticles, a process for their preparation, and an adhesive composition which adheres strongly to surfaces of dental materials, such as dentin, enamel, metal, ceramics, and polymeric material, without prior etching or priming of the surfaces.

DETAIL DESCRIPTION OF THE INVENTION

The invention provides a dental composition including a nanoparticle having an acidic polymerizable siloxane moiety. Preferably the dental composition polymerizes to form a polymeric dental material having an adhesion to dentin of at least 10 MPa.

A preferred composition of the invention is a dental adhesive composition which is an aqueous mixture of particles having acidic moieties. These mixtures are in the form of solutions or dispersions which have a pH in the range of from 1 to 6, preferably from 2 to 4. Acidic moiety, as used herein, refers to a moiety which is an acid moiety, an ester of an acid moiety or a salt of an acid moiety. Compounds containing at least one acidic moiety, as used herein, refers to compounds containing at least one acid moiety, ester of an acid moiety or salt of an acid moiety. Compounds containing acidic moieties, as used herein, refers to compounds containing two or more of: acid moiety, ester of an acid moiety and/or salt of an acid moiety. For example compounds containing two or more acid moieties, and compounds containing an ester of an acid moiety and a salt of an acid moiety.

The nanoparticles may subsequently be polymerized in the dental adhesive composition of the invention whereby a crosslinked network of particles is formed. Alternatively, the nanoparticles may be copolymerized with one or more polymerizable monomer components whereby a polymerized matrix of the monomer component is formed wherein the dispersed nanoparticles are cross-linked to the matrix. The incorporation of the nanoparticles into the polymerized matrix of the monomer component according to the invention provides a cured dental adhesive composition having increased strength and decreased polymerization shrinkage, while the dental composition has the same or only slightly increased viscosity as compared to the same composition not containing nanoparticles.

The dental adhesive composition according to the invention is hydrolysis stable, self-etching, self-priming and shows excellent adhesive properties. The composition of the invention contains an aqueous phase in an amount of 90 to 10% by weight. Optionally, the aqueous phase may comprise one or more organic solvents. The organic solvent may be any solvent acceptable in the dental field, which is miscible with water. Specific examples of the organic solvent which may be contained in the aqueous phase of the composition of the invention are selected from the group of acetone, ethanol, isopropanol, tert.-butanol, ethylacetate. Preferably a polar aprotic or protic solvent such as acetone, ethanol, or tert.-butanol is used. The optional organic solvent may be a mixture of different solvents.

The composition of the invention contains polymerizable nanoparticles containing acidic moieties. The nanoparticles are present in an amount of from 10 to 90% by weight of the composition. Preferably, the polymerizable nanoparticles are present in an amount of at least 30, more preferably at least 50% by weight.

The polymerizable nanoparticles containing acidic moieties are obtainable by hydrolysis of a mixture containing one or more hydrolyzable organosilicon compounds. The hydrolyzable organosilicon compounds are compounds which may undergo condensation reactions so as to form aggregates containing Si—O—Si-bond, whereby organic group, preferably polymerizable organic groups are exposed on the surface of the aggregate.

The nanoparticles are formed in situ, preferably in an aqueous component containing further components of the dental adhesive composition whereby it is not necessary to isolate and re-disperse the nanoparticles in a dental composition. Moreover, the particles according to the invention may be used without further saturation of remaining condensable groups with monofunctional triorganosilyl groups for avoiding condensation between particles. Thereby, the process of the invention provides a particle composition in a one-pot reaction without the need for complicated, energy- and time-consuming reaction-steps. The nanoparticles are dispersed in the aqueous phase in a stable and homogenous manner whereby agglomeration of the nanoparticles to aggregates is avoided.

The hydrolysis of the hydrolyzable siloxane groups in a dispersion, leads to particles having a narrow particle size distribution and a well-defined structure with Si—O—Si bonds and peripherally exposed polymerizable organic moieties and active acidic moieties. Preferably, the nanoparticles formed according the invention have an average particle size of from 1 to 20 nm, most preferably of from 1 to 5 nm. The size of the nanoparticles may be controlled by the choice of the type and amount of the hybrid monomer component as well as the presence of further co-hydrolyzable components.

The average particle size of the nanoparticles is below 50 nm. Preferably, the average particle diameter of the nanoparticles is in a range of from 1 to 50 nm, more preferably in a range of from 1 to 20 nm. The nanoparticles contain acidic moieties preferably on the surface of the particles. Moreover, the nanoparticles contain polymerizable groups exposed on the surface of the particles.

In the mixture from which polymerizable nanoparticles containing acidic moieties according to the invention may be obtained, contain two portions of hydrolyzable organosilicon compounds. In the first portion of the hydrolyzable organic silicon compounds, polymerizable groups are present. This portion may contain one or more compounds containing a polymerizable group. The polymerizable group is preferably an acrylate or metacrylate containing residue.

The second portion contains hydrolyzable organosilicon compounds which have one or more acidic moieties. The acidic moieties may be selected from the group of sulfonic acid, and phosphonic acid derivative. The second group may contain one or more organosilicon compounds.

The mixture may contain compounds which belong either into the first portion (i) or to the second portion (ii) or to both portions of hydrolyzable organosilicon compounds. Specifically an organosilicon compound may contain only polymerizable groups whereby it belongs to the portion (i). Alternatively, an organosilicon compound may contain one or more acidic moieties whereby it belongs to portion (ii). Alternatively, an organosilicon compound may contain both one or more polymerizable groups and one or more acidic moieties whereby this compound belongs to portion (i) and (ii). The mixture may further contain hydrolyzable compounds which neither belong to portion (i) nor portion (ii). Specific examples are organosilicon compounds or metal compounds selected from the group of alkoxides or metal complexes such as metal acetyl acetonates whereby the metals are selected from the group of Ba, Al, La, Ti, Zr, Tl, In or other transition elements or elements of lanthanides or actines.

In a specific embodiment of the present invention, portion (i) and (ii) contain the same compounds, i.e. the hydrolyzable organosilicon compounds contain one or more polymerizable group and one or more acidic moieties. Preferred compounds are siloxane compounds within the scope of the following formulas and salts thereof:

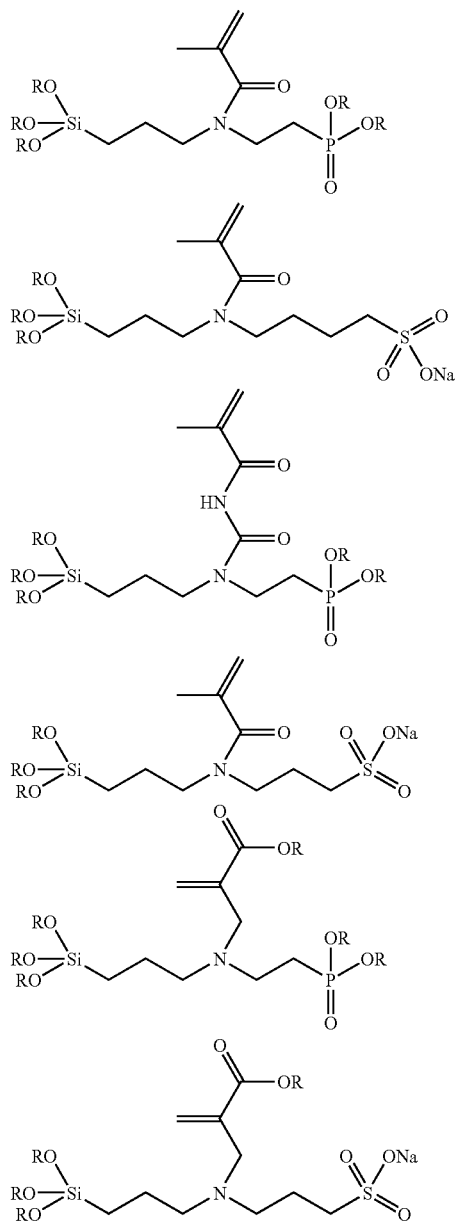

wherein each R independently is hydrogen, a substituted or unsubstituted alkyl group having from 1 to 20 carbon atoms, a substituted or unsubstituted alkenyl group having from 2 to 20 carbon atoms, a substituted or unsubstituted alkylaryl group having from 5 to 20 carbon atoms, a substituted or unsubstituted aryl group having from 5 to 20 carbon atoms or a substituted or unsubstituted heteroaryl group having from 5 to 20 carbon atoms. Alkyl as used herein includes linear, breached and cyclic alkyl groups. Alkenyl as used herein includes linear, breached and cyclic alkenyl groups.

Alternatively, the polymerizable nanoparticles are obtainable by co-condensation of an organosilicon-methylene oxo acryl ester and the following phosphonic ester or sulfonic acid salt compounds and subsequent hydrolysis of phosphonic ester groups or ion exchange of the sulfonic acid salts:

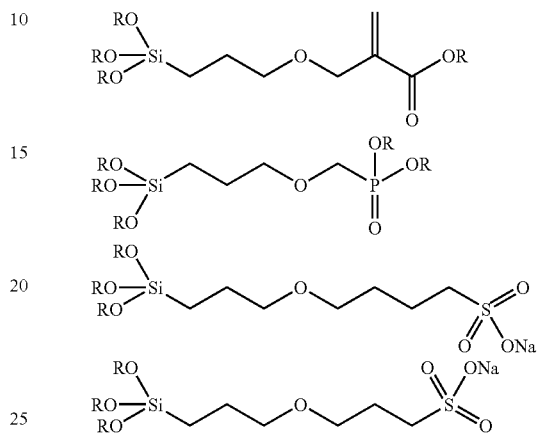

wherein each R independently is hydrogen, a substituted or unsubstituted alkyl group having from 1 to 20 carbon atoms, a substituted or unsubstituted alkenyl group having from 2 to 20 carbon atoms, a substituted or unsubstituted alkylaryl group having from 5 to 20 carbon atoms, a substituted or unsubstituted aryl group having from 5 to 20 carbon atoms or a substituted or unsubstituted heteroaryl group having from 5 to 20 carbon atoms.

The mixture may further contain hydrolyzable siloxane components that contain no polymerizable groups such as tetraethoxy silane, tetramethoxy silane, monomethyl triethoxy silane, monomethyl trimethoxy silane, dimethyl diethoxy silane, dimethyl dimethoxy silane or tetrachloro silane. The mixture may further contains metal compounds selected from the group of alkoxides or metal complexes such as metal acetyl acetonates whereby the metals are selected from the group of Ba, Al, La, Ti, Zr, Tl, In or other transition elements or elements of the lanthanides or actinides. In the presence of such metal compounds, the hydrolysis provides cocondensates of the hydrolyzable siloxane compound and the metal compound. The use of an additional metal compound will usually lead to an increase of the average particle size whereby an increasing amount of the additional metal compound will increase the average particle size of the particles. The cocondensation of the nanoparticles in the presence of metal compounds will provide nanoparticles having wherein the metal compounds are predominantly present in the core portion of the particle.

In order to increase the etch activity organic and/or inorganic acids such as itaconic acid, maleic acid, phosphoric acid, phosphonic acid and sulfonic acid are present in the dental adhesive composition of the invention. Preferably, the total amount of acid is up to 30% by weight of the composition.

In a further preferred embodiment, the composition further comprises an initiator, co-initiator and inhibitor. Preferably, the initiator, co-initiator and inhibitor are present in a total amount of 0.01 to 5% by weight. The polymerization initiator may be a thermal initiator, a redox-initiator or a photo initiator. Preferably, the polymerization initiator and/or sensitizer is a photoinitiator, such as benzoinmethylether, benzilketal, camphorquinone or acrylphosphinoxide. Alternatively, the polymerization initiator is a redox initiator such as dibenzoylperoxide/aromatic or aliphatic tert. amine, tert. butyl peroxy benzoate/ascorbic acid/metal compound.

The composition according to the invention may further containing nanofillers. The hydrolysis stable organosilicon based adhesive of the invention may further contain one or more non-polymerizable nanofillers with an average particle size of 1 to 50 nm to increase abrasion resistance and mechanical properties. The composition of the invention may also contain anti-microbial compounds such as trichlosane or chlorohexidine.

The composition according to the invention may be a one component adhesive composition or a two pack system adapted to provide adhesive composition upon mixing of the packs. In a two pack system, the initiator, co-initiator and inhibitor are preferably separated from the polymerizable component of the composition. The composition according to the invention preferably provides an adhesion to dentine of at least 10 MPa.

Alkylenes as used herein, refers to compounds having one or more moieties containing a —C=C— group. Substituted as used herein, refers to replacement of one or more hydrogen(s) by a halogen(s), hydroxyl(s), and/or amine(s). For example, substituted alkylene includes, alkylene moieties having at least one halogen, hydroxyl or amine, and includes alkylene moieties having more than one halogen, hydroxyl and/or amine. $C_n$, as used herein, refers to a moiety containing n carbon(s), wherein n is an integer.

The present invention also relates to nanoparticles obtainable by hydrolysis of a mixture containing one or more hydrolyzable organosilicon compounds wherein (i) at least a portion of the hydrolyzable organosilicon compounds contains one or more polymerizable groups and (ii) at least a portion of the hydrolyzable organosilicon compounds contain one or more acidic moieties.

Preferably, portion (i) and (ii) contain the same compounds. The mixture preferably contains one or more siloxane compounds within the scope of the following formulas:

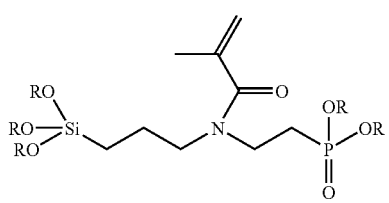

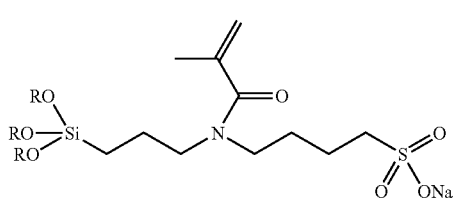

-continued

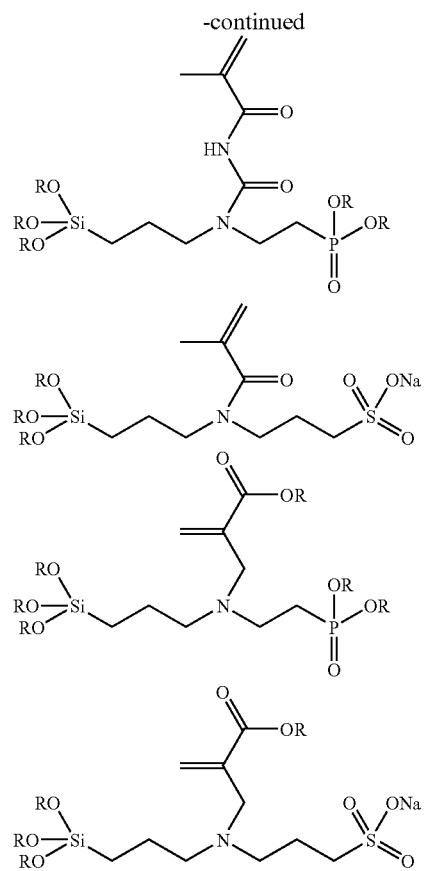

wherein each R independently is hydrogen, a substituted or unsubstituted alkyl group having from 1 to 20 carbon atoms, a substituted or unsubstituted alkenyl group having from 2 to 20 carbon atoms, a substituted or unsubstituted alkylaryl group having from 5 to 20 carbon atoms, a substituted or unsubstituted aryl group having from 5 to 20 carbon atoms or a substituted or unsubstituted heteroaryl group having from 5 to 20 carbon atoms.

Alternatively, the nanoparticles according to the invention are obtainable by co-condensation of an organosilicon -methylene oxo acryl ester and the following phosphonic ester or sulfonic acid salt compounds and subsequent hydrolysis of phosphonic ester groups or ion exchange of the sulfonic acid salts:

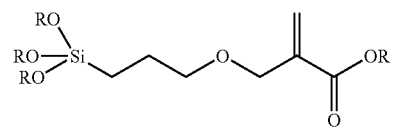

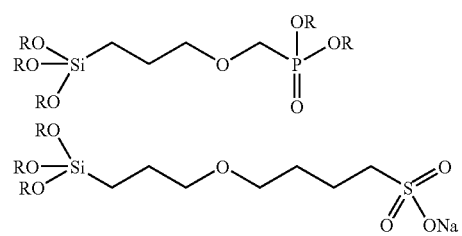

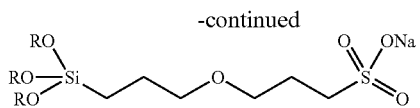

wherein each R independently is hydrogen, a substituted or unsubstituted alkyl group having from 1 to 20 carbon atoms, a substituted or unsubstituted alkenyl group having from 2 to 20 carbon atoms, a substituted or unsubstituted alkylaryl group having from 5 to 20 carbon atoms, a substituted or unsubstituted aryl group having from 5 to 20 carbon atoms or a substituted or unsubstituted heteroaryl group having from 5 to 20 carbon atoms.

The nanoparticles may be obtained by hydrolysis of a mixture further containing metal compounds selected from the group of alkoxides or metal complexes such as metal acetyl acetonates whereby the metals are selected from the group of Ba, Al, La, Ti, Zr, Tl, In or other transition elements or elements of the lanthanides or actinides and/or hydrolyzable siloxane components that contain no polymerizable groups such as tetraethoxy silane, tetramethoxy silane, monomethyl triethoxy silane, monomethyl trimethoxy silane, dimethyl diethoxy silane, dimethyl dimethoxy silane or tetrachloro silane. The nanoparticles of the invention preferably have an average particle size of from 1 to 20 nm, more preferably from 1 to 5 nm.

The nanoparticles of the invention are preferably characterized by the following formula:

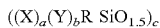

wherein

X, which may be the same or different, is a polymerizable group selected of the group of -methylene oxo acryl ester, acryl amides, acryl urethanes, acryl ureas, acryl thiourethanes, acryl thioureas;

Y, which may be the same or different, is an acidic moiety selected from the group of phosphonic and sulfonic acids or salts thereof;

a and b each independently is an integer from 1 to 10;

c is a number from 1 to 1000.000;

and R is a group having a valence of a+b+1.

Preferably, X is selected from

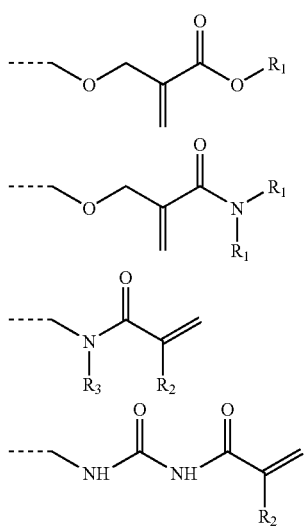

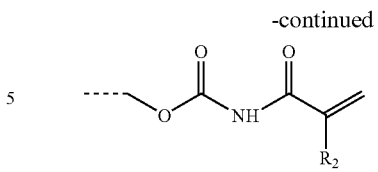

wherein each $R_1$ independently is hydrogen, a substituted or unsubstituted alkyl group having from 1 to 20 carbon atoms, a substituted or unsubstituted alkenyl group having from 2 to 20 carbon atoms, a substituted or unsubstituted alkenyloxyalkenyl group having from 2 to 20 carbon atoms, a substituted or unsubstituted alkylaryl group having from 5 to 20 carbon atoms, a substituted or unsubstituted aryl group having from 5 to 20 carbon atoms or a substituted or unsubstituted heteroaryl group having from 5 to 20 carbon atoms.

each $R_2$ independently is hydrogen, a monofunctional substituted or unsubstituted alkyl group having from 1 to 20 carbon atoms, a substituted or unsubstituted alkenyl group having from 2 to 20 carbon atoms, a substituted or unsubstituted alkylaryl group having from 5 to 20 carbon atoms, a substituted or unsubstituted aryl group having from 5 to 20 carbon atoms or a substituted or unsubstituted heteroaryl group having from 5 to 20 carbon atoms.

each $R_3$ independently is hydrogen, a substituted or unsubstituted alkyl group having from 1 to 20 carbon atoms, a substituted or unsubstituted alkenyl group having from 2 to 20 carbon atoms, a substituted or unsubstituted alkenyloxyalkenyl group having from 2 to 20 carbon atoms, a substituted or unsubstituted alkylaryl group having from 5 to 20 carbon atoms, a substituted or unsubstituted aryl group having from 5 to 20 carbon atoms or a substituted or unsubstituted heteroaryl group having from 5 to 20 carbon atoms.

The present invention also relates to a process for the preparation of nanoparticles, which comprises the step of hydrolysis in the presence of an acid or base, and a fluoride ion source of a mixture containing one or more hydrolyzable organosilicon compounds wherein (i) at least a portion of the hydrolyzable organosilicon compounds contains one or more polymerizable groups and wherein (ii) at least a portion of the hydrolyzable organosilicon compounds contain one or more acidic moieties.

Preferably, the fluoride ion source is ammonium fluoride.

The present invention also relates to siloxane compounds within the scope of the following formulas and salts thereof:

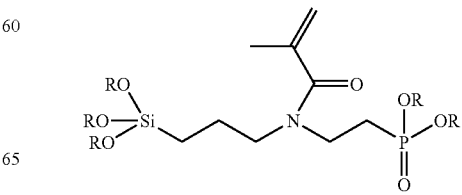

-continued

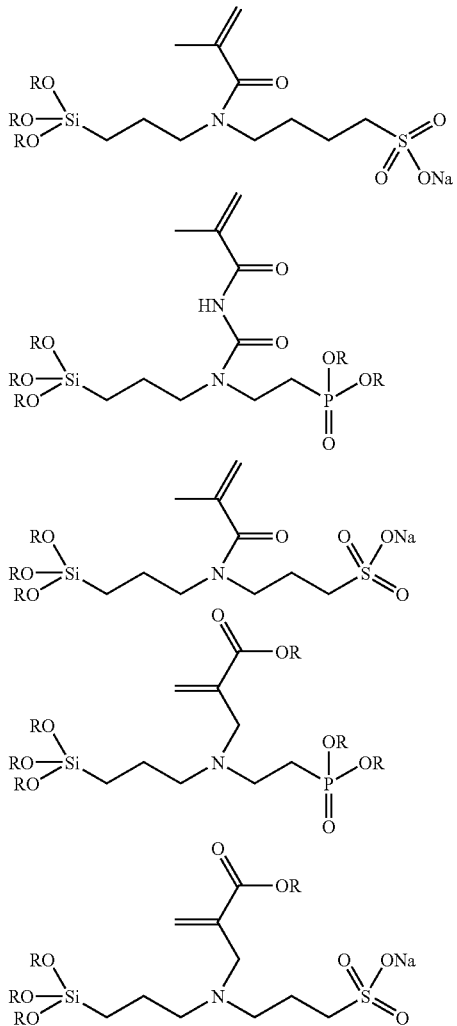

wherein each R independently is hydrogen, a monofunctional substituted or unsubstituted alkyl group having from 1 to 20 carbon atoms, a substituted or unsubstituted alkenyl group having from 2 to 20 carbon atoms, a substituted or unsubstituted alkylaryl group having from 5 to 20 carbon atoms, a substituted or unsubstituted aryl group having from 5 to 20 carbon atoms or a substituted or unsubstituted heteroaryl group having from 5 to 20 carbon atoms.

The siloxane compound of the invention may be employed for the preparation of nanoparticles. The nanoparticles may be used for the preparation of a dental composition. Preferably, the dental composition is a hydrolysis stable, self-etching, self-priming dental adhesive composition.

Specific examples show, that nanoparticles form in the presence of other hydrolyzable siloxane components that contain no polymerizable groups such as tetraethoxy silane, tetramethoxy silane, monomethyl triethoxy silane, monomethyl trimethoxy silane, dimethyl diethoxy silane, dimethyl dimethoxy silane or tetrachloro silane. The use of an additional silane compound will usually lead to an increase of the average particle size whereby an increasing amount of the additional silane compound will increase the average particle size of the particles. The cocondensation of the nanoparticles in the presence of silane compounds will provide nanoparticles wherein the silane compounds are predominantly present in the core portion of the particle.

The invention is illustrated by the following examples.

EXAMPLE 1

Preparation of Poly[N-(ethyl phosphonic acid)-N-methacrylamido-propyl]siloxane

N-(diethyl ethyl phosphonate)-aminopropyltriethoxysilane 26.973 g (0.122 mol) of diethyl vinylphosphonate were added slowly under ice cooling and stirring to 20.000 g (0.122 mol) 3-aminopropyl triethoxy silane so that the temperature did not rise above 80° C. Subsequently, the mixture was stirred for one day at 60° C. The resulting product is soluble in solvents such as water, methanol, chloroform, DMF and THF.

Yield: 46.97 g (100% of th.)

($C_{15}H_{36}NO_6PSi$), 385.51

$^{13}$C-NMR: 59.6 (8), 59.5 (3), 56.5 (6), 56.4 (7), 50.5 (5), 41.5 (2), 16.6 (9), 14.8/14.7 (4), 6.3 (1) ppm

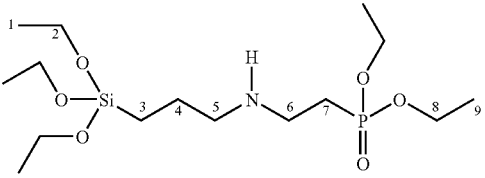

wherein the numbering system (1,2,3,4,5,6,7,8 and 9) shown is referenced in the above C-NMR data, but otherwise may be disregarded.

N-(diethyl ethyl phosphonate)-N-methacrylamido-propyltriethoxysilane 38.699 g (0.100 mol) N-(diethyl ethyl phosphonate)-aminopropyltriethoxy silane were dissolved in 100 ml methylene chloride in a 3-necked 250-ml-flask. The 3-necked 250-ml-flask had was equipped with a magnet stirrer, a thermometer and a 50 ml dropping funnel. After cooling to 0–5° C. 11.710 g (0.105 mol) methacryloylisocyanate dissolved in 50 ml methylene chloride was added to the 3-necked 250-ml-flask while stirring for 1.5 hours so that the temperature remains at 0–10° C. Then the reaction mixture was stirred at 23° C. over night. Thereafter, the mixture was extracted twice with 100 ml H$_2$O, dried over NaSO$_4$, filtered off and 0.050 g of 2,6-di-tert.-butyl-p-cresol was added to the solution. The methylene chloride was removed at 40° C. in vacuum and the product was dried.

The product had solubility in: Methanol, CHCl$_3$, and in Acetone.

The product yield was: 41.6 g (83.4% of theoretical)

$_{23°\ C.}$=5.711±0.139 Pa*s ($C_{20}H_{41}O_8N_2PSi$), 496.61

IR: 3228 (NH), 1714 (CO), 1634 (C=C), 1481 (CH$_2$) cm$^{-1}$ $^{13}$C-NMR: 167.3 (11), 152.5 (10), 139.4/139.5 (12), 121.2/120.6 (13), 61.3 (8), 57.9 (2), 45.9 (5), 41.4 (6), 24.8 (7), 22.6 (7), 20.2 (3), 18.0 (14), 17.7 (9),15.8 (4), 6.9 (1)

The structural formula of the product is as follows:

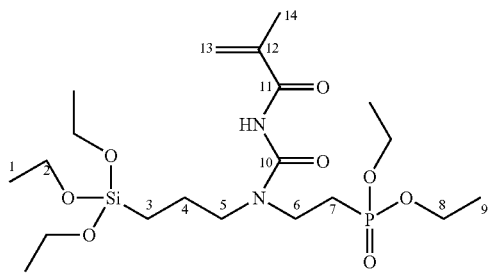

wherein the numbering system (1,2,3,4,5,6,7,8,9,10,11,12, 13 and 14) shown is referenced in the above C-NMR data, but otherwise may be disregarded.

Poly[N-(diethyl ethyl phosphonate)-N-methacrylamido-propyl]siloxane

To 45.200 g (0.091 mol) N-(diethyl ethyl phosphonate)-N-methacrylamido-propyltriethoxy silane dissolved in 100 ml Acetone were added 5.079 g HF solution composed of 4.915 (0.273 mol) water and 0.164 g (0.008 mol) HF under stirring. The reaction mixture were stirred for additional 20 hours at ambient temperature. Then the solvent and ethanol were removed in vacuum and the nanoparticles were dried at 40° C. at 8 mbar. The nanoparticles are soluble in methanol, chloroform and acetone.

Yield: 32.0 g (91.2% of th.)

Average particle size: 3.2 nm $C_{14}H_{26}N_2O_{6.5}PSi$, 385.43

IR: 3228 (NH), 1714 (CO), 1634 (C=C), 1481 ($CH_2$) $cm^{-1}$

Poly[N-(ethyl phosphonic acid)-N-methacrylamido-propyl]siloxane

In a 4-necked 1-l-flask equipped with a stirrer, a thermometer, refluxer with $CaCl_2$-drying tube and 50 ml dropping funnels 32.000 g (0.083 mol) Poly[N-(diethyl ethyl phosphonate)-N-methacrylamido-propyl]siloxane were dissolved in 100 ml of methylene chloride. Then 13.982 g (0.091 mol) Trimethylbromsilane was added drop by drop over a period of 20 minutes under stirring. Thereafter the reaction mixture was stirred for an additional 2 hours. By adding 100 ml of methanol the phosphonic acid silyl esters were hydrolyzed. Prior to removing the solvents 0.032 g (0.145 mol) BHT was added and the product was dried at 40° C. in vacuum. The nanoparticles are soluble in methanol, ethanol, and in a solution of 50 percent by weight ethanol and 50 percent by weight water having a pH-value of 1.5.

Yield: 29.0 g (98.3% of th.)

$(C_{10}H_{18}N_2O_{6.5}PSi)_n$, $(329.32)_n$

IR: 3228 (NH), 1714 (CO), 1634 (C=C), 1481 ($CH_2$) $cm^{-1}$ $^{13}$C-NMR: 169.1 (11), 153.0 (10), 140.4 (12), 123.1 (13), 62.4 (7), 42.7 (5), 39.5 (6), 18.2 (14), 16.5 (4), 14.3 (3)

The general structural formula of Poly[N-(ethyl phosphonic acid)-N-methacrylamido-propyl]siloxane is as follows:

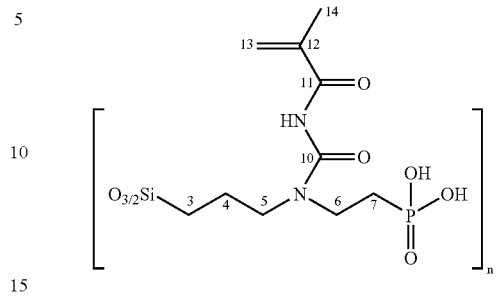

wherein n is an integer greater than 1, and 3/2 refers to the presence of 2 or 3 oxygen atoms.

Application Example 1 (Dental Adhesive)

To a cleaned dentin tooth surface with a rubber cup were applied some drops of a solution composed of 0.5 g poly[N-(ethyl phosphonic acid)-N-methacrylamido-propyl]siloxane dissolved in 2 ml of an ethanol/water-mixture (in a 1:1 weight ratio). The applied drops remained for 20 seconds. Then the solvent was removed by blowing gently with air from a dental syringe for at least 5 seconds and polymerized by light-cure for 10 seconds to form a light-cured polymeric layer. Thereafter, Spectrum light curable composite restorative, sold by Dentsply International Inc., was applied over the polymeric layer and light cured. After storage for 24 hours at 37° C. an adhesion of composite restorative to dentin of 10 MPa was measured.

It should be understood that while the present invention has been described in considerable detail with respect to certain specific embodiments thereof, it should not be considered limited to such embodiments but may be used in other ways without departure from the spirit of the invention and the scope of the appended claims.

What is claimed is:

1. A composition comprising: nanoparticles, each said nanoparticles comprising a siloxane moiety, said siloxane moiety having at least one acidic moiety and at least one polymerizable moiety.

2. The composition of claim 1 wherein said composition is a dental composition and said nanoparticles are soluble in a solvent selected from the group consisting of ethanol, acetone, isopropanol, tert-butanol, and ethylacetate.

3. The composition of claim 1 wherein said composition further comprises an aqueous phase.

4. The composition of claim 1 wherein said composition is a hydrolysis stable, self-etching, self-priming dental adhesive composition, and said composition comprises from 90 to 10 percent by weight of an aqueous phase, and from 10 to 90 percent by weight of said nanoparticles.

5. The composition of claim 1 wherein said composition further comprises from 0.01 to 5 percent by weight of a polymerization initiator.

6. The composition of claim 1, wherein said composition further comprises an organic solvent.

7. The composition of claim 1 further comprising an acid.

8. The composition of claim 7 wherein said acid comprises up to 30 percent by weight of said composition.

9. The composition of claim 1 wherein the nanoparticles are prepared from a mixture comprising hydrolyzable organosilicon compounds within the scope of one of the following formulas or a salt thereof:

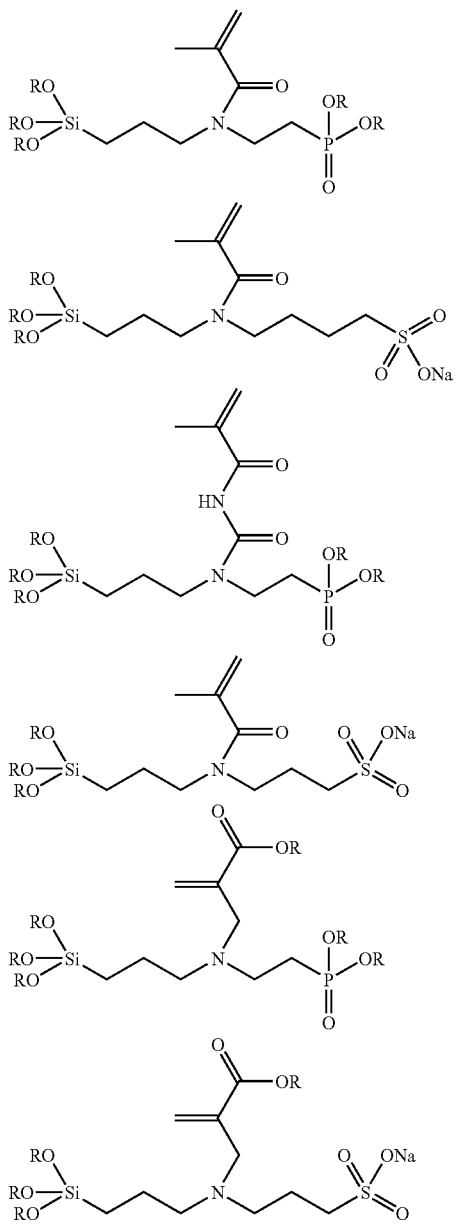

wherein each R independently is hydrogen, a substituted or unsubstituted alkyl group having from 1 to 20 carbon atoms, a substituted or unsubstituted alkenyl group having from 2 to 20 carbon atoms, a substituted or unsubstituted alkylaryl group having from 5 to 20 carbon atoms, a substituted or unsubstituted aryl group having from 5 to 20 carbon atoms or a substituted or unsubstituted heteroaryl group having from 5 to 20 carbon atoms.

10. The composition of claim 9 wherein the mixture further comprises a metallic agent selected from the group of alkoxide, metal complex, Ba, Al, La, Ti, Zr, Ti, In, lanthanide and actinide.

11. The composition of claim 9 wherein the mixture further comprises a hydrolyzable organosilicon compound that does not have a polymerizable group.

12. The composition of claim 1 wherein said nanoparticles have an average particle size of from 1 to 20 nm.

13. The composition of claim 1 wherein said nanoparticles have an average particle size of from 1 to 5 nm.

14. The composition of claim 1 further comprising a solvent selected form the group consisting of acetone, ethanol and tert.-butanol.

15. The composition of claim 1 further comprising an acid selected form the group consisting of itaconic acid, maleic acid, phosphoric acid, phosphonic acid, and sulfonic acid.

16. The composition of claim 1 further comprising a polymerization initiator selected form the group consisting of thermal initiator, redox-initiator and photoimtiator.

17. The composition of claim 1 further comprising benzoinmethylether, benzilketal, camphorquinone or acrylphosphinoxide.

18. The composition of claim 1 further comprising a redox initiator.

19. The composition of claim 1 further comprising non-reactive nanofillers.

20. The composition of claim 1, further comprising an anti-microbial compound.

21. A composition comprising a nanoparticle formed by hydrolysis of a mixture comprising one or more hydrolyzable organosilicon compounds wherein (i) at least a portion of the hydrolyzable organosilicon compounds have one or more polymerizable groups and wherein (ii) at least a portion of the hydrolyzable organosilicon compounds have one or more acidic moieties.

22. The composition of claim 21 wherein the mixture contains a hydrolyzable organosilicon compound within the scope of one of the following formulas:

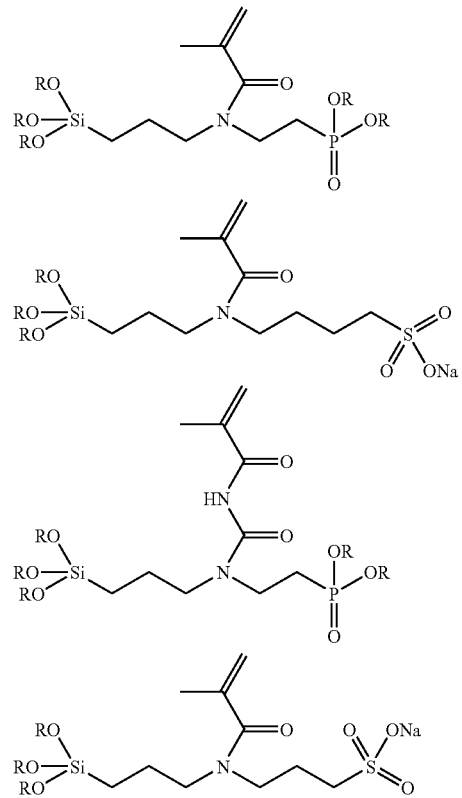

-continued

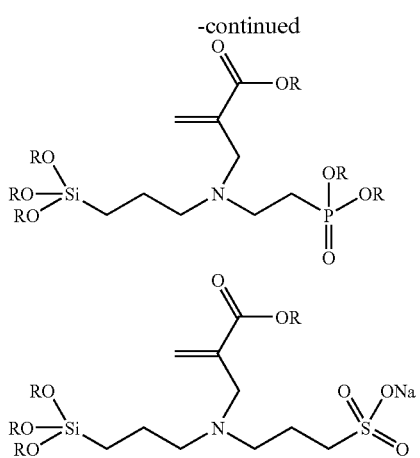

wherein each R independently is hydrogen, a substituted or unsubstituted alkyl group having from 1 to 20 carbon atoms, a substituted or unsubstituted alkenyl group having from 2 to 20 carbon atoms, a substituted or unsubstituted alkylaryl group having from 5 to 20 carbon atoms, a substituted or unsubstituted aryl group having from 5 to 20 carbon atoms or a substituted or unsubstituted heteroaryl group having from 5 to 20 carbon atoms.

23. The composition of claim 21 wherein the polymerizable nanoparticles and formed by co-condensation of an organosilicon.-methylene oxo acryl ester and a phosphonic ester within the scope of one of the following general formulas or a sulfonic acid salt compound, and subsequent hydrolysis of phosphonic ester groups or ion exchange of the sulfonic acid salts:

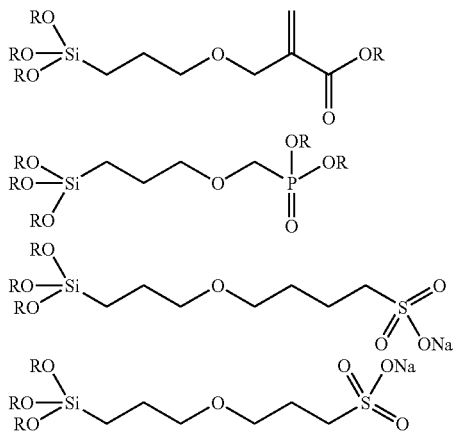

wherein each R independently is hydrogen, a substituted or unsubstituted alkyl group having from 1 to 20 carbon atoms, a substituted or unsubstituted alkenyl group having from 2 to 20 carbon atoms, a substituted or unsubstituted alkylaryl group having from 5 to 20 carbon atoms, a substituted or unsubstituted aryl group having from 5 to 20 carbon atoms or a substituted or unsubstituted heteroaryl group having from 5 to 20 carbon atoms.

24. The composition of claim 21 wherein the mixture further comprises a metallic agent selected from the group consisting of alkoxides and complexes of the lanthanide and actinide series.

25. A composition comprising: nanoparticles, each of said nanoparticles comprising at least one moiety within the scope of the following formula:

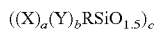

wherein each X, independently, is a polymerizable group selected from the group consisting of methylene acryl ester, acryl amide, acryl urethane, acryl urea, acryl thiourethane, and acryl thiourea;
each Y, independently, is an acidic moiety selected from the group consisting of phosphonic acid, sulfonic acid, salt of phosphonic acid and salt of sulfonic acid;
a organic bridging and b are each independently an integer from 0 to 10;
c is a number of from 1 to 1000; and
R is a group having a valency of a+b+1.

26. The composition of claim 25 wherein X is selected from the group consisting of

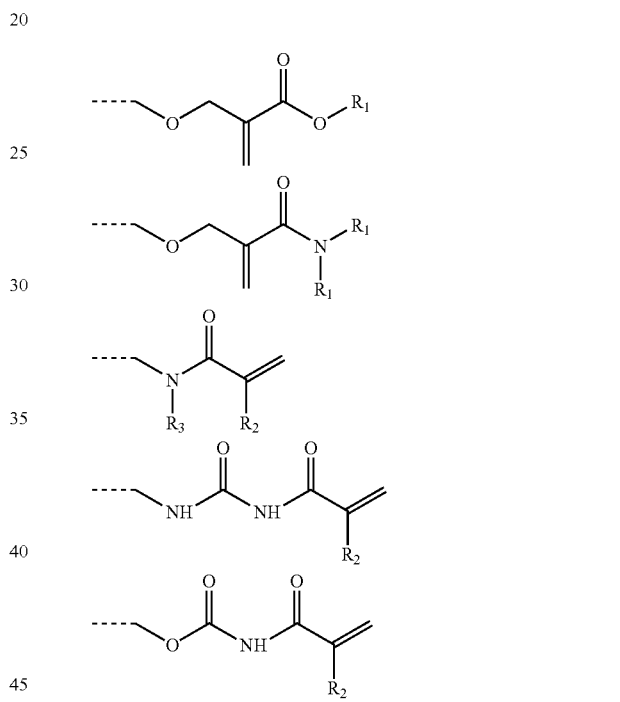

wherein each $R_1$ independently is hydrogen, a substituted or unsubstituted alkyl group having from 1 to 20 carbon atoms, a substituted or unsubstituted alkenyl group having from 2 to 20 carbon atoms, a substituted or unsubstituted alkyloxy group having from 1 to 20 carbon atoms, a substituted or unsubstituted alkenyloxy group having from 2 to 20 carbon atoms, a substituted or unsubstituted alkylaryl group having from 6 to 20 carbon atoms, a substituted or unsubstituted aryl group having from 5 to 20 carbon atoms or a substituted or unsubstituted heteroaryl group having from 5 to 20 carbon atoms,
each $R_2$ independently is hydrogen, a monofunctional substituted or unsubstituted alkyl group having from 1 to 20 carbon atoms, a monofunctional substituted or unsubstituted alkenyl group having from 2 to 20 carbon atoms, a substituted or unsubstituted alkylaryl group having from 6 to 20 carbon atoms, a substituted or unsubstituted aryl group having from 5 to 20 carbon atoms or a substituted or unsubstituted heteroaryl group having from 5 to 20 carbon atoms, R₃ is hydrogen, a substituted or unsubstituted alkyl group having from 1 to 20 carbon atoms, a substituted or unsubstituted alkenyl group having from 2 to 20 carbon atoms, a substituted or unsubstituted alkyloxyalkyl group having from 1 to 20 carbon atoms, a substituted or unsubstituted alkenyloxyalkenyl group having from 2 to 20 carbon atoms, a substituted or unsubstituted alkylaryl group having from 6 to 20 carbon atoms, a substituted or unsubstituted aryl group having from 5 to 20 carbon atoms or a substituted or unsubstituted heteroaryl group having from 5 to 20 carbon atoms.

27. A hydrolyzable organosilicon compound within the scope of one of the following general formulas:

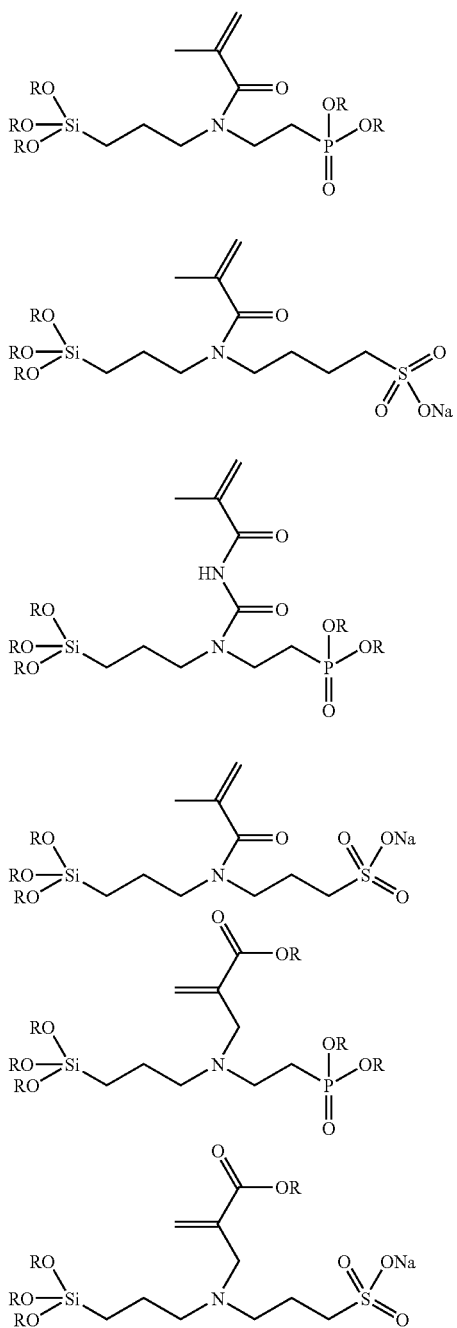

wherein each R independently is hydrogen, a substituted or unsubstituted alkyl group having from 1 to 20 carbon atoms, a substituted or unsubstituted alkenyl group having from 2 to 20 carbon atoms, a substituted or unsubstituted alkylaryl group having from 5 to 20 carbon atoms, a substituted or unsubstituted aryl group having from 5 to 20 carbon atoms or a substituted or unsubstituted heteroaryl group having from 5 to 20 carbon atoms.

28. A dental method comprising: providing a hydrolysis stable, self-etching, self-priming dental adhesive composition comprising an aqueous phase, and acidic polymerizable siloxane nanoparticles having at least one acidic moiety and at least one polymerizable moiety, and applying said composition to a natural dental tooth.

29. The method of claim 28 wherein said composition polymerizes to form a polymeric material having an adhesion to dentin of at least 10 MIPa.

30. The method of claim 28 wherein said acidic polymerizable siloxane nanoparticles are made by co-condensation of an organosilicon-methylene oxo acryl ester and a phosphonic ester or sulfonic acid salt compound within the scope of one the following general formulas and subsequent hydrolysis of phosphonic ester groups or ion exchange of the sulfonic acid salts:

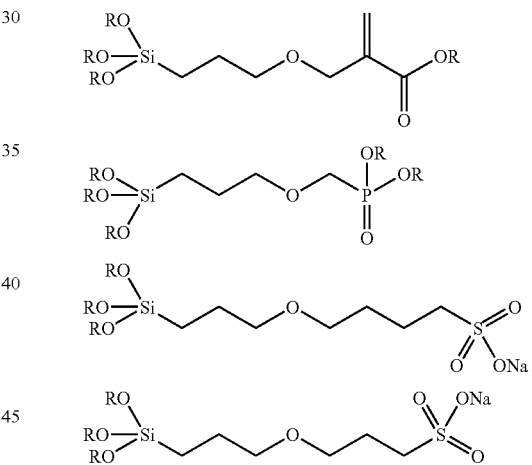

wherein each R independently is hydrogen, a substituted or unsubstituted alkyl group having from 1 to 20 carbon atoms, a substituted or unsubstituted alkenyl group having from 2 to 20 carbon atoms, a substituted or unsubstituted alkylaryl group having from 5 to 20 carbon atoms, a substituted or unsubstituted aryl group having from 5 to 20 carbon atoms or a substituted or unsubstituted heteroaryl group having from 5 to 20 carbon atoms.

31. The method of claim 28 wherein said acidic polymerizable siloxane nanoparticles are prepared by hydrolysis in the presence of an acid or base, and a fluoride ion source of a mixture containing one or more hydrolyzable organosilicon compounds wherein (i) at least a portion of the hydrolyzable organosilicon compounds contains one or more polymerizable groups and wherein (ii) at least a portion of the hydrolyzable organosilicon compounds contain one or more acidic moieties.

32. The method of claim 31 wherein the fluoride ion source is ammonium fluoride.

33. The method of claim 31 wherein the nanoparticles have an average particle diameter of from 1 to 20 nm.

34. A composition according to claim 1 wherein the nanoparticles are soluble in at least one solvent selected from the group consisting of methanol, chloroform, and acetone.

35. The composition of claim 10 wherein the metal is selected from the group consisting of Ba, Al, Ti, Zr, Tl, In, lanthanide metals, and actinide metals.

* * * * *